United States Patent [19]

Mezei et al.

[11] Patent Number: 4,485,054
[45] Date of Patent: Nov. 27, 1984

[54] METHOD OF ENCAPSULATING BIOLOGICALLY ACTIVE MATERIALS IN MULTILAMELLAR LIPID VESICLES (MLV)

[75] Inventors: Michael Mezei; Fredric J. Nugent, both of Halifax, Canada

[73] Assignee: Lipoderm Pharmaceuticals Limited, Nova Scotia, Canada

[21] Appl. No.: 432,686

[22] Filed: Oct. 4, 1982

[51] Int. Cl.$^3$ ............... A61K 9/50; B01J 13/02
[52] U.S. Cl. ..................... 264/4.6; 424/38; 424/182; 424/1.1; 428/402.2; 436/829
[58] Field of Search ............... 264/4.6; 424/38; 436/829

[56] References Cited

U.S. PATENT DOCUMENTS

| | | |
|---|---|---|
| 3,804,776 | 4/1974 | Yazawa et al. |
| 4,016,100 | 4/1977 | Suzuki et al. |
| 4,053,585 | 10/1977 | Allison et al. |
| 4,078,052 | 3/1978 | Papahadjopoulos |
| 4,089,801 | 5/1978 | Schneider |
| 4,217,344 | 8/1980 | Vanlerberghe et al. |
| 4,224,179 | 9/1980 | Schneider |
| 4,235,871 | 11/1980 | Papahadjopoulos et al. |
| 4,342,826 | 8/1982 | Cole .................... 436/829 X |

OTHER PUBLICATIONS

Bangham, A. D., Standish M. M., and Watkins, J. C., "Diffusion of Univalent Ions Across the Lamellae of Swollen Phospholipids", *J. Mol. Biol.*, 13: 238-252, 1965.
Batzri, S. and Korn, E. D., "Single Bilayer Liposomes Prepared Without Sonication", *Biochim. Biophys. Acta.*, 298: 1015-1019, 1973.
Mezei, M. and Gulasekharam, V., "Liposomes–A Selective Drug Delivery System for the Topical Roue of Administration", *Life Sciences*, vol. 26, pp. 1473-1477, 1980.
Szoka, F. and Papahadjopoulos, D., "Comparative Properties and Methods of Preparation of Lipid Vesicles (Liposomes)", *Ann. Rev. Biophys. Bioeng.*, 9: 467-508, 1980.
Zumbuehl, O. and Weder, H. G., "Liposomes of Controllable Size in the Range of 40 to 180 nm by Defined Dialysis of Lipid/Detergent Mixed Micelles", *Biochim. Biophys. Acta.*, 640: 252-262, 1981.

*Primary Examiner*—Richard D. Lovering
*Attorney, Agent, or Firm*—Banner, Birch, McKie and Beckett

[57] ABSTRACT

This invention provides an improved procedure for producing large multilamellar lipid vesicles (MLV), which may be used to encapsulate a biologically active material, particularly lipophilic substances. According to this invention, a lipid film is formed on inert, solid contact masses within a vessel, by evaporating an organic solvent therefrom. Subsequent agitation in the presence of an aqueous liquid, followed by a period in which the vessel remains undisturbed yields the multilamellar vesicles. The procedure permits the encapsulation of both hydrophilic and lipophilic materials.

15 Claims, No Drawings

METHOD OF ENCAPSULATING BIOLOGICALLY ACTIVE MATERIALS IN MULTILAMELLAR LIPID VESICLES (MLV)

TECHNICAL FIELD

The present invention relates to the art of liposomal encapsulation. More specifically, the present invention relates to an improved procedure for producing large multilamellar lipid vesicles (MLV), which may be used to encapsulate a biologically active material, particularly lipophilic substances.

BACKGROUND ART

Liposomes or lipid vesicles are onion-like structures comprising a series of bimolecular lipid layers spaced from one another by an aqueous solution, the outermost layer being lipid. Liposomes have been advantageously used to encapsulate biologically active materials for a variety of uses. The prior art describes a number of techniques for producing synthetic liposomes. Most of these techniques relate to the formation of unilamellar vesicles. For example, U.S. Pat. No. 4,078,052 - Papahadjopoulos describes a procedure for producing large unilamellar vesicles (LUV). This particular procedure, however, is restricted to the lipid phosphalidyserine which was found to uniquely form the intermediate cochleate structure, apparently essential to the formation of the large lipid vesicles, in the presence of calcium cations.

A variety of other techniques have also been disclosed for producing small unilamellar vesicles (SUV). In one approach, a mixture of the lipid and an aqueous solution of the material to be encapsulated is warmed and then subjected to vigorous agitation and ultrasonic vibration. In another approach, U.S. Pat. No. 4,089,801 - Schneider, a mixture of a lipid, an aqueous solution of the material to be encapsulated, and a liquid which is insoluble in water is subjected to ultrasonication, whereby aqueous globules encased in a monomolecular lipid layer are formed dispersed in the water-insoluble liquid. The lipid vesicles are then formed by combining the first dispersion with a second aqueous fluid and then subjecting the mixture to centrifugation, whereby the globules are forced through the monomolecular lipid layer dividing the two phases, thereby forming the bimolecular lipid layer characteristic of liposomes. In still another approach, (O. Zumbuehl and H. G. Weder, Biochim. Biophys. Acta., 640: 252–262, 1981), the lipids and additives are solubilized with detergents by agitation or sonication, yielding defined mixed micelles. The detergents are then removed by dialysis.

Two alternate methods for the preparation of small unilamellar vesicles (SUV) that avoid the need for sonication are the ethanol injection technique (S. Batzri and E. D. Korn, Biochim. Biophys. Acta 198: 1015–1019, 1973) and the ether-infusion technique (D. Deamer and A. D. Bangham, Biochim. Biophys. Acta 443: 629–634, 1976). In these processes, the organic solution of lipids is rapidly injected into a buffer solution where it spontaneously forms liposomes.

A more recent method for preparing large unilamellar lipid vesicles (LUV) is the reverse phase evaporation technique described in U.S. Pat. No. 4,235,871 - Papahadjopoulos. This technique consists of forming a water-in-oil emulsion of (a) the lipids in an organic solvent and (b) the substances to be encapsulated in an aqueous buffer solution. Removal of the organic solvent under reduced pressure produces a mixture having a gel-like character which can then be converted to the lipid vesicles by agitation or by dispersion in an aqueous media.

U.S. Pat. No. 4,016,100 - Suzuki et al describes still another method of entrapping certain biologically active materials in unilamellar lipid vesicles by freezing an aqueous phospholipid dispersion of the biologically active materials and lipids.

For a comprehensive review of methods for preparing liposomes refer to a recent publication by Szoka and Papahadjopoulos (Ann. Rev. Biophys. Bioeng. 9: 467–508, 1980).

Methods for producing multilamellar lipid vesicles (MLV), are described by Bangham et al (J. Mol. Biol. 13: 238–252, 1965) and by Mezei and Gulasekharam, (Life Sci., 26: 1473–1477, 1980). The lipids and lipophilic substances are first dissolved in an organic solvent. The solvent is then removed under reduced pressure by rotary evaporation. The lipid residue forms a thin film on the wall of the container. Upon the addition of an aqueous solution, generally containing electrolytes or hydrophilic biologically active materials, large multilamellar lipsomes are formed. Small unilamellar vesicles can be prepared by sonication of the large multilamellar vesicles.

Most of these processes suffer from either low encapsulation efficiency or limitations in the types of materials that can be encapsulated or both. For example, most of these processes are limited to the encapsulation of hydrophilic materials, and cannot efficiently accommodate the encapsulation of lipophilic substances. Moreover, all of the currently available procedures, except the ones described by Bangham et al and by Mezei and Gulasekharam, are only suitable for the encapsulation of biologically active materials in oligolamellar, or unilamellar liposomes.

It is an object of the present invention to provide a process for encapsulating biologically active materials in large multilamellar lipid vesicles.

It is another object of this invention to provide a method for encapsulating biologically active materials that results in a significant increase in the encapsulation efficiency thereof.

It is still another object of this invention to provide a method of encapsulating biologically active materials in large multilamellar lipid vesicles that is not limited with respect to the material to be encapsulated and can efficiently accommodate both lipophilic and hydrophilic substances.

It is a further object of this invention to provide a procedure for encapsulating biologically active materials in a multilamellar lipid vesicle that can be conducted on a larger scale relative to prior art procedures.

DISCLOSURE OF THE INVENTION

These and other objects are met by the present invention which comprises a process for producing large multilamellar lipid vesicles comprising the steps of:

(a) providing a vessel partially filled with inert, solid contact masses;

(b) providing a lipid component dissolved in a suitable organic solvent within the vessel;

(c) removing the organic solvent by evaporation so as to form a thin lipid film on the inner wall of the vessel and on the surfaces of the contact masses;

(d) thereafter adding an aqueous liquid to the vessel and agitating the vessel to form an aqueous dispersion of lipid; and (e) allowing the dispersion to stand essentially undisturbed for a time sufficient for the multilamellar vesicles to form.

If desired, the aqueous dispersion of the large multilamellar lipid vesicles can be further treated; for example, ultrasonication or filtration can be used to reduce the size of the vesicles or to change their structure to oligolamellar or unilamellar structures.

According to a known procedure, the multilamellar vesicles can be filtered through a series of polycarbonate filters, having decreasing pore sizes, so as to form the unilamellar vesicles.

It is specifically contemplated that hydrophilic and/or lipophilic biologically active substances will be encapsulated within the vesicles. A particularly advantageous consequence of the large-sized vesicles produced by this invention is that the risk of percutaneous transfer of the formulation is substantially reduced or eliminated. Therefore, this invention is particularly useful for encapsulating lipid soluble medicaments intended to produce local (i.e., topical) rather than systemic action.

As used in the specification and claims, the terms "biologically active material" or "biologically active substance" means a compound or composition which, when present in an effective amount, produces an effect in living cells or organisms.

DETAILED DESCRIPTION

As disclosed, this process differs from the technique proposed by Bangham in that the lipid film forming step is conducted in a vessel partially filled with inert, solid contact masses. This modification has a significant and unexpected impact on the overall encapsulation procedure. In particular, we have observed a significant increase in encapsulation efficiency, especially in the encapsulation of lipophilic substances.

Significant variation is possible in the size, size distribution, shape and composition of the contact masses. The principal characteristics of the contact masses are: (1) that the contact masses be inert to the materials used in the formulation, in other words there should be no unwanted interaction between the contact masses and the lipid, lipophilic substances, organic solvent or aqueous liquid employed, and (2) that the contact masses be solid throughout the processing steps, in other words the contact masses should not dissolve or disintegrate and should provide an appropriate solid surface for supporting the thin lipid film. Prior experimental testing has used glass beads or balls as the inert, solid contact masses and these materials have proven to be particularly suitable. It is also expected that metal balls, e.g., stainless steel and synthetic substances, e.g., plastics, will also be suitable in appropriate circumstances. While spherical contact masses are preferred, since they provide the maximum surface area in a given volume and are easily fluidized during the agitation step, other regular and irregular shapes could also be used.

The size of the contact masses used in any application will depend upon the scale of operation, the intensity of agitation and other factors that will be apparent to one skilled in this art. As an example, it is normally appropriate to use contact masses having a size such that the ratio of the vessel volume to the volume of an individual contact mass is between 50 and 50,000. Generally, spherical contact masses will have a diameter between 1.0 mm and 100 mm. It is also contemplated that the contact masses could have a range or distribution of sizes. However, our test work has shown that equally sized contact masses adequately satisfy the requirements of the invention. The number of contact masses employed will depend upon their shape and size, the size of the vessel, the volume of organic solvent used and the quantity of lipid and lipophilic substances dissolved. An appropriate number is used for increasing the surface area during the evaporation step and increasing the total area of the thin lipid film formed, but reserving sufficient volume within the vessel for movement of the contact masses during the agitation step.

The lipid vesicles of the present invention can be produced from phospholipids, neutral lipids, surfactants or any other related chemical compounds having similar amphiphilic properties. As is well known, these materials can be classified according to the formula A-B where A is a hydrophilic, generally polar group, e.g., a carboxyl group, and B is a hydrophobic, i.e., lipophilic, non-polar group, e.g., a long chain aliphatic hydrocarbon group. Suitable lipids include phosphatidylcholines, phosphatidylethanolamine, phosphatidylserine, phosphatidylinositol, lysophosphatidylcholine and phosphatidylglycerol. In addition, other lipophilic additives may be used for selectively modifying the characteristics of the lipid vesicle, e.g., the stability and permeability of the vesicle membrane. Such other substances include stearylamine, phosphatidic acid, dicetyl phosphate, tocopherol, cholesterol, and lanolin extracts. From the foregoing, it should be appreciated that the composition of the lipid component can be substantially varied without significantly reducing the improvement in encapsulation efficiency provided by the present invention, and other lipids, in addition to those listed above, can be used as desired.

According to the present invention, the lipid component, together with any other lipophilic substances including biologically active materials, is initially dissolved in a suitable, generally non-polar, organic solvent. The organic solvent must be capable of being substantially removed from the lipid by evaporation and must not otherwise affect any of the lipophilic substances included in the formulation. Representative solvents include: ethers, esters, alcohols, ketones and various aromatic and aliphatic hydrocarbons, including fluorocarbons. The solvents may be used alone or in combination; for example, a 2:1 mixture of chloroform and methanol has been found to be suitable. The organic solvent is removed by evaporation, which can conveniently be accomplished by use of a rotary evaporator at temperatures generally between 20° and 60° C. and under a less-than-atmospheric pressure. As is well known, the evaporative conditions will strongly depend upon the physical properties of the organic solvent and the lipophilic materials used in the formulation.

After the lipid film forming step, the lipids are hydrated with an aqueous liquid to form an aqueous dispersion of lipid. The required agitation can be accomplished by the rotation or translation, i.e., vibration, of the vessel. An important feature of the present invention is that the presence of the inert, solid contact masses within the vessel provides an increased and consistent level of mechanical agitation, which enhances the formation of uniformly sized lipid vesicles. As is well known, this hydration step is conducted above the transition temperature of the lipid components.

The aqueous liquid may be pure water; but will generally be an aqueous solution of an electrolyte or a biologically active material. For example, an aqueous solution of sodium chloride or calcium chloride may be imployed. Additionally, active substances including pharmaceuticals such as, vitamins, hormones, enzymes, antibiotics and bactericides, and cosmetics such as, dyestuffs, perfumes and humectants may be included.

While most of the prior art procedures are limited to encapsulating hydrophilic materials, the present invention can also accomodate the encapsulation of hydrophobic, i.e., lipophilic materials. Testing has shown that lypophilic medicaments, e.g. progesterone, can be encapsulated at high efficiencies.

In other words, the present invention can be advantageously employed to encapsulate either hydrophilic or lipophilic substances or both. In the case of lipophilic materials, the substances to be encapsulated are co-dissolved with the lipids in the organic solvent prior to the lipid film forming step; while as noted above hydrophilic substances are conveniently added to the aqueous liquid used to disperse the lipid film.

After agitating the lipid-aqueous liquid mixture, the resulting dispersion is then allowed to remain undisturbed for a time sufficient to allow the lipid vesicles to form and mature. Generally, it will be sufficient to allow the vessel to stand undisturbed at room temperature for approximately one to two hours. The aqueous dispersion of the multilamellar lipid vesicles can then be recovered from the vessel containing the inert, solid contact masses. If desired, any non-incorporated active substances can be removed from the dispersion using known techniques such as repeated centrifugations, dialysis or column chromatography. The lipid vesicles can then be resuspended in any suitable electrolytic buffer for subsequent use.

Since the procedure described by Bangham is the only prior art process of which we are aware for encapsulating lipophilic materials in large multilamellar lipid vesicles, we conducted a series of experiments directly comparing the process of the present invention with the Bangham procedure. In particular, we compared the two procedures so as to determine their relative effectiveness in encapsulating lipophilic substances. The following examples will vividly demonstrate the significant and unexpected improvement in the encapsulation efficiency of lipophilic materials made possible by the present invention.

EXAMPLE I

In this example, multilamellar lipid vesicles are prepared using the procedure of this invention (Method A) and the procedure disclosed by Bangham (Method B). The materials used in preparing the lipid vesicles and the amounts thereof are listed below in Table 1. A small amount of progesterone labelled with Carbon 14 was mixed with a quantity of non-radioactive progesterone to facilitate the determination of its encapsulation efficiency.

TABLE 1

| | |
|---|---|
| DL alpha dipalmitoyl phosphatidyl choline (DPPC) | 22.2 mg |
| Cholesterol | 5.0 mg |
| Progesterone (containing 0.5 uCi; $^{14}$C) | 5.0 mg |
| Calcium chloride solution (8 mM) | 5.0 ml |

In accordance with the method of this invention, Method A, the DPPC, cholesterol and progesterone were co-dissolved in a chloroform-methanol solvent (2:1) in a 50 ml round bottom vessel. Glass beads, having a diameter of 5 mm, were added to the vessel and the solvent was evaporated under vacuum in a rotary evaporator, thereby leaving a thin lipid film on the glass beads and on the vessel wall. A warm calcium chloride solution at 65° C. was then added to the vessel, and the mixture was vigorously shaken for one minute. Afterwards, the vessel was further agitated by rotating it in the rotary evaporator, without applying a vacuum, at 65° C. for 30 minutes. The resultant dispersion was allowed to stand for one hour.

According to the Bangham procedure, Method B, the DPPC, cholesterol and progesterone were similarly dissolved in a chloroform-methanol solvent (2:1) within a 50 ml round bottom vessel. The vessel did not contain any contact masses. The organic solvent was evaporated under vacuum in a rotary evaporator until a smooth, dry lipid film was observed on the wall of the vessel. A calcium chloride solution, heated to a temperature of 65° C. was then added to the contents of the vessel and the mixture was vigorously shaken in a 65° C. water bath for 30 minutes. The resultant dispersion was then allowed to stand for one hour.

After allowing the newly formed liposomal preparations to stand at room temperature for one hour, small aliquots (approximately 10 μl) of each of the preparations were examined under a microscope with a magnification of 475X using polarized light to verify the formation of the large multilamellar vesicles. The remaining portions of the liposomal preparations were filtered through polycarbonate filters having an 8 μm pore size. The filtrates were then centrifuged at 22,000 Xg for 15 minutes at 20°C. The supernatant was decanted and the centrifugate was resuspended in 5 ml of 8 mM aqueous calcium chloride solution. This procedure was repeated twice. The centrifugate separated from the final step of centrifugation was resuspended in 5.0 ml of 8 mM aqueous calcium chloride solution, and 10 μl aliquots from each preparation were used to calculate the encapsulation efficiency. The results are presented in Example III.

EXAMPLE II

The procedure of Example I was repeated three additional times, but in each case the formulation was changed to that listed in Tables 2, 3 and 4, respectively. In formulating the liposomes from the substances listed in Table 4, a 1000 ml vessel was substituted for the 50 ml vessel.

TABLE 2

| | |
|---|---|
| Phosphatidylcholine (purified) | 22.2 mg |
| Cholesterol | 5.0 mg |
| Progesterone (0.5 uCi; $^{14}$C) | 5.0 mg |
| Calcium Chloride (8 mM) | 5.0 ml |

TABLE 3

| | |
|---|---|
| Dipalmitoyl phosphatidylcholine | 22.2 mg |
| Cholesterol | 5.0 mg |
| Stearylamine | 2.0 mg |
| Progesterone (0.5 uCi; $^{14}$C) | 5.0 mg |
| Calcium Chloride (8 mM) | 5.0 ml |

TABLE 4

| | |
|---|---|
| Dipalmitoyl phosphatidylcholine | 888.0 mg |
| Cholesterol | 200.0 mg |
| Progesterone (1.0 uCi: $^{14}$C) | 200.0 mg |
| Calcium Chloride (8 mM) | 200.0 ml |

EXAMPLE III

The progesterone encapsulation efficiencies, using the test procedures described in Examples I and II, are listed in Table 5. As shown by these results, the present invention (Method A) provides a substantial and unexpected increase in the encapsulation efficiency of lipophilic materials as compared with the prior art (Method B) available for accomplishing the same result.

TABLE 5

| TABLE FORMULATION | % of Encapsulation Method A | % of Encapsulation Method B |
|---|---|---|
| 1 | 77.0 | 7.8 |
| 2 | 83.0 | 6.1 |
| 3 | 87.0 | 10.0 |
| 4 | 85.0 | 4.5 |

In addition to enchancing encapsulation efficiency, the present invention also makes it possible to produce liposomes on a larger scale. The Bangham method can only produce small batches of liposomes (e.g., 100–200 ml) otherwise the encapsulation efficiency substantially decreases. The batch size when using our invention, however, can be significantly increased simply by increasing the surface area of the vessel and the inert, solid contact masses. This result is evidenced by the encapsulation efficiency data in Table 5 for the formulation of Table 4, in which a 1000 ml vessel was substituted for the 50 ml vessel used in the prior tests. This vessel also contained a larger amount of solid inert contact masses, providing much greater surface area for the lipid film formation. Consequently, the present invention makes the large scale manufacturing of liposomes possible.

While preferred embodiments of this invention have been discussed herein, those skilled in the art will appreciate that changes and modifications may be made without departing from the spirit and scope of this invention, as defined in and limited only by the scope of the appended claims.

We claim:

1. A process for producing large multilamellar lipid vesicles comprising the steps of:
   (a) providing a vessel partially filled with inert, solid contact masses;
   (b) providing a lipid component dissolved in a suitable organic solvent within said vessel;
   (c) removing the organic solvent by evaporation so as to form a thin lipid film on the inner wall of said vessel and on the surfaces of said contact masses;
   (d) thereafter adding an aqueous liquid to said vessel and agitating same to form an aqueous dispersion of lipid; and
   (e) allowing said dispersion to stand essentially undisturbed for a time sufficient for the multilamellar vesicles to form.

2. The process of claim 1 wherein the lipid component is a phospholipid.

3. The process of claim 2 wherein the phospholipid is selected from the group consisting of phosphatidylcholines, lysophosphatidylcholine, phosphatidylserine, phosphatidylethanolamine, and phosphatidylinositol.

4. The process of claim 3 wherein the phospholipid is provided in admixture with cholesterol.

5. The process of claim 3 wherein the phospholipid is provided in admixture with stearylamine or phosphatidic acid.

6. The process of claim 1 wherein a lipophilic biologically active material is provided in admixture with the lipid component.

7. The process of claim 6 wherein the lipophilic biologically active material comprises steroid hormones.

8. The process of claim 7 wherein the steroid hormone is progesterone.

9. The process of claim 1 where in the organic solvent is selected from the group consisting of chloroform, methanol and mixtures thereof.

10. The process of claim 1 where in the aqueous liquid contains a hydrophilic biologically active material.

11. The process of claim 1 wherein the inert, solid contact masses are made from glass, metal or a synthetic plastic.

12. The process of claim 11 wherein the inert, solid contact masses are spherical.

13. The process of claim 12 wherein the spherical, inert, solid contact masses have a diameter between 1 mm and 100 mm.

14. The process of claim 1 wherein the aqueous dispersion of lipid is allowed to stand essentially undisturbed for about 1 to 2 hours.

15. In a process for producing large multilamellar lipid vesicles of the type wherein a thin lipid film is formed on the inner wall of a vessel, an aqueous liquid is added to the vessel, the vessel is agitated to form an aqueous dispersion of lipid and the dispersion is allowed to stand essentially undisturbed for a time sufficient for the multilamellar vesicles to form, the improvement comprising also forming said thin lipid film on the surface of inert solid contact masses which partially fill said vessel.

* * * * *